United States Patent [19] [11] 4,416,274
Jacobsen et al. [45] Nov. 22, 1983

[54] ION MOBILITY LIMITING IONTOPHORETIC BIOELECTRODE

[75] Inventors: Stephen C. Jacobsen, Salt Lake City; Richard D. Luntz, Murray, both of Utah

[73] Assignee: Motion Control, Inc., Salt Lake City, Utah

[21] Appl. No.: 236,753

[22] Filed: Feb. 23, 1981

[51] Int. Cl.³ ............................................. A61M 15/08
[52] U.S. Cl. ....................................... 604/20; 128/803
[58] Field of Search ................... 128/207.21, 639, 640, 128/641, 793, 798, 802, 803, 303.13

[56] References Cited

U.S. PATENT DOCUMENTS 3,567,657  3/1971  Lichtenstein ........................ 128/639
3,848,600  11/1974  Patrick et al. ................... 128/303.13
4,033,334  7/1977  Fletcher et al. ..................... 128/639
4,164,226  8/1979  Tapper ................................ 128/798
4,250,878  2/1981  Jacobsen et al. ................ 128/207.21

FOREIGN PATENT DOCUMENTS 2440836  3/1976  Fed. Rep. of Germany ...... 128/639
2727396  12/1978  Fed. Rep. of Germany .
WO80/00988  3/1981  PCT Int'l Appl. ................. 128/639

Primary Examiner—C. Fred Rosenbaum
Assistant Examiner—T. J. Wallen
Attorney, Agent, or Firm—Thorpe, North & Western

[57] ABSTRACT

A bioelectrode for use in the iontophoretic delivery of ions into the skin or tissue of a person includes either a receptacle or a composition of material suitable for holding ions to be delivered, a metallic foil disposed on one side of the receptacle or composition of matter, and a coupling device for electrically coupling the foil to an electrical source. The other side of the receptacle or composition of material is for placement against a person's skin or tissue so that ions may be delivered thereinto. The receptacle or composition of material both include features or characteristics which inhibit the migration of ions laterally therein, i.e., in a direction generally parallel to the surface of the skin or tissue, but which allow migration in a direction generally perpendicular to the surface of the skin or tissue, and in particular from the metal foil toward the person's skin or tissue. The advantage of this capability is to provide a substantially uniform movement of ions into the skin or tissue over surface area of contact of the bioelectrode with the skin.

13 Claims, 7 Drawing Figures

ION MOBILITY LIMITING IONTOPHORETIC BIOELECTRODE

BACKGROUND OF THE INVENTION

This invention relates to an iontophoretic bioelectrode method and apparatus and more particularly to such a method and apparatus in which migration of ions from the apparatus to a person's skin or skin barrier is inhibited in certain directions.

Iontophoresis is a technique of delivering ions into a person's skin or tissue by placing a solution or other medium containing the ions in contact with the skin, and applying electric current to the medium. The solution or medium containing the ions is typically carried by a first bioelectrode pouch or receptacle. Ions are caused to migrate from the ion carrying medium through the skin or tissue by the application of the electric current to the medium, and by placement against the skin of a second bioelectrode within some proximity of the first bioelectrode and the application of current of opposite polarity to the second bioelectrode. This technique has been discussed in a number of prior art patents including U.S. Pat. No. 4,141,359 and 4,166,457. Examples of bioelectrodes which are generally useful for making electrical contact with the skin are described in U.S. Pat. Nos. 3,862,633, 3,945,384 and 3,973,557.

There have been several bioelectrode proposals for carrying the ion solution or medium and placing it in proximity with the skin including provision of a receptacle with a wetable barrier on one side thereof. The wetable barrier or wall is covered until time of use and then uncovered for placement against the skin. Then, upon application of the electrical current, the ions migrate through the wall into the skin.

Another proposed arrangement involves the use of a receptacle having a microporous membrane on one side thereof which may be placed in contact with a person's skin. The membrane is selected so that it will not leak prior to use, but will allow migration of ions therethrough to the skin upon application of an electric current to the ion-carrying solution. With this arrangement, less care need be given to storage, transport and use of the receptacle since the ion containing fluid will not leak as it is used.

One of the principal problems with the prior art devices has been the problem of the bioelectrode producing burns at the site of application of medications. If the current to the bioelectrode is too high, the resistance of the skin or tissue may result in burns or other tissue damage. Further, once the skin or tissue is burned, the resistance at the site of the burn decreases allowing for an increase in current flow and thus ion migration at that site and this compounds the danger of serious burns to the skin or tissue. If a blemish or cut exists somewhere at the location of contact of the bioelectrode with the skin or tissue, then the ions tend to migrate toward and concentrate at the blemish thereby increasing the danger of a burn at that site.

One approach to reducing the likelihood of burns to the skin or tissue is to simply reduce the amount of current applied to the bioelectrode. This, however, increases the treatment time for the patient since lower current flow requires longer periods of application to reach the same degree of ion penetration. Of course, it would be desirable to both minimize the treatment time and minimize the likelihood of burns to the patient from the treatment.

SUMMARY OF THE INVENTION

It is an object of the invention to provide a new and improved bioelectrode for use in the iontophoretic delivery of ions into the skin or tissue of a person.

It is another object of the invention to provide such as bioelectrode in which the likelihood of burns to the skin or tissue is reduced.

It is a further object of the invention to provide such a bioelectrode wherein the lateral mobility of the ions in the electrode is inhibited.

It is an additional object of the invention to provide a bioelectrode for delivering ions into the skin or tissue of a person uniformly over a certain skin or tissue surface area regardless of local variations in skin impedance such as that caused by previous tissue damage.

It is also an object of the invention, in accordance with one aspect thereof to provide a bioelectrode adapted to minimize the chance of chemically induced iontophoretic ph burns.

The above and other objects of the invention are realized in a bioelectrode structure which includes a holder for holding ions to be delivered, one side of which is for placement against the person's skin or tissue. The holder is adapted to inhibit movement of ions in a direction generally parallel to the surface of the skin or tissue while allowing movement toward the side which is placed against the skin or tissue. Also included is an electrically conductive sheet of material attached to and covering a substantial portion of the other side of the holder, and an electrical conductor coupled to the sheet of material for connection to an electrical source.

Electrical current is supplied by the conductor to the sheet of material to cause the ions contained in the holder to migrate towards the side of the holder in contact with the skin. Since lateral movement of ions is inhibited by the holder (due to the longer current path lengths), the likelihood of burning is decreased since movement of ions to concentrate at one place is inhibited.

The holder can be adapted to inhibit the lateral movement of ions either by including structure within the holder to physically guide the ions or by proper selection and dimensioning of the ion holding material to enhance migration in one direction while inhibiting migration in another direction. An example of the latter is gel material preloaded with ions. By Incorporation of an appropriate phosphate buffer in the gel material, chemically induced iontophoretic ph burns can better be avoided.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
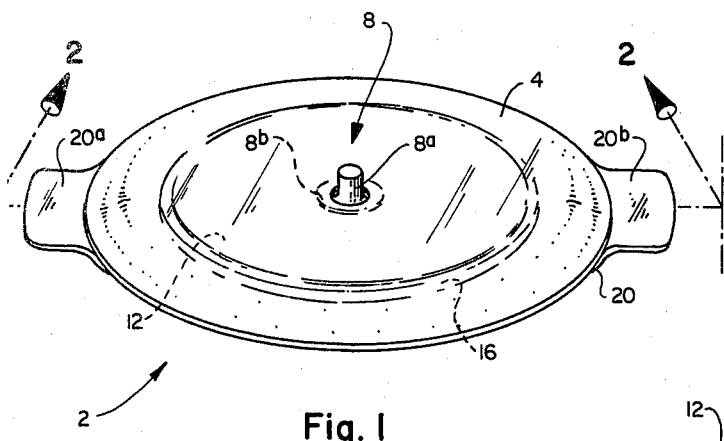
FIG. 1 is a perspective view of a bioelectrode made in accordance with the principles of the present invention.
Figure 2:
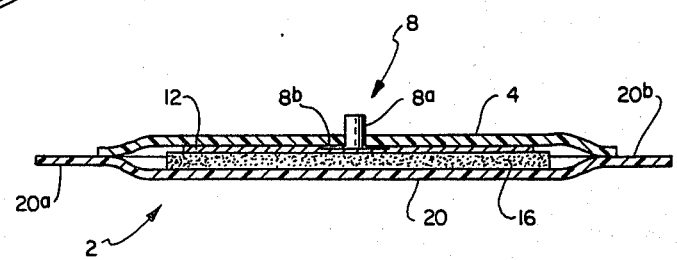
FIG. 2 is a side, cross-sectional view of the bioelectrode of FIG. 1.

Referring to the drawings there are shown several embodiments of an iontophoresis device made in accordance with the present invention. FIGS. 1 and 2 show a bioelectrode 2 composed of an upper cover 4 which may be made of plastic, treated paper, or other suitable covering material. Mounted in the cover 4 is the male part 8 of a conventional metallic snap used on clothing and the like. The snap 8 includes an upwardly projecting nipple 8a which protrudes through the cover 4 so that contact may be had with the corresponding female part of the snap or other suitable conductor. The nipple 8a is joined to a base portion 8b which is disposed on the underneath side of the cover 4.

Affixed to the underneath side of the cover 4 in contact with the base portion 8b of the snap 8 is a piece of flexible foil 12 made of aluminum or other electrically conductive material. The foil 12 is in electrical contact with the snap 8 so that any electrical current applied to the snap 8 will flow to the foil 12. Affixed to the underneath side of the foil 12 is a sheet of iontophoresis gel 16 such as karaya gum, other polysacharide gels, or similar hydrophillic aqueous gels capable of carrying ions. Specific examples of such gels include polyvinyl alcohol, polymethyl pyrollidine, methyl cellulose, polyacrylamide, polyhemas, and polyhema derivatives, etc. The perimeter of the gel 16 is substantially coterminous with the foil 12 as shown in the drawings. The gel selected should have nonirritating properties to avoid irritating the person's skin or tissue, suitable viscosity and surfactant properties to obtain good electrical contact with the skin or tissue, and the ability to act as a carrier medium for the ions. The lower surface of the gel 16 is for placement in contact with a person's skin or tissue for the iontophoretic treatment.

In order to minimize the chance of chemically induced iontophoretic ph burns in the surface tissues and the underlying tissues in the area of placement of the device, a phosphate buffer, such as mono-basic and/or di-basic sodium phosphate, is included in the gel material 16. Advantageously, a ph of about six will be provided in the gel.

The gel 16 is dimensioned so that ion migration is enhanced in a direction normal to the person's skin or tissue, and generally inhibited in a direction parallel to the person's skin. It has been found that a thickness-to-width ratio of about 0.1 facilitates such control of the migration of ions. These controls on ion migration are desirable to provide a more uniform transfer of ions from the entire bottom surface area of the gel into the person's skin. That is, ion migration is stimulated to take place from the gel 16 over the shortest path to the skin, and migration laterally of ions to points of high current intensity for delivery into the skin is avoided.

A bottom cover 20 is placed in contact with the lower surface of the gel material 16 until time of use of the bioelectrode to keep the gel free from contamination. The upper cover 4 and lower cover 20 thus completely enclose the gel material 16 until the bioelectrode is to be used. Then, the bottom cover 20 is simply peeled from the gel material and the gel material is placed in contact with the patient's skin or tissue. The cover 20 may be made of any suitable material such as plastic, treated paper, etc., which will maintain the gel material 16 free from contamination. Ears 20a and 20b are formed in the cover 20 to extend outwardly beyond the perimeter of the upper cover 4 to facilitate peeling the bottom cover from the gel material 16.

In use, the bioelectrode of FIGS. 1 and 2 is prepared with the ionic medicament carried in the gel material 16. The bioelectrode would then be delivered in a form generally as shown in the drawings and used as needed. In such use, as explained in the aforecited patents and in copending patent application, Ser. No. 963,029, the bioelectrode of FIG. 2 would be placed against a person's skin with the gel material 16 in contact with the skin. Another electrode would be placed against the skin at a location spaced from the first electrode. Appropriate electric potentials would then be applied to electrodes to create a potential gradient between the electrode carrying the medicament and the skin.

Figure 3:
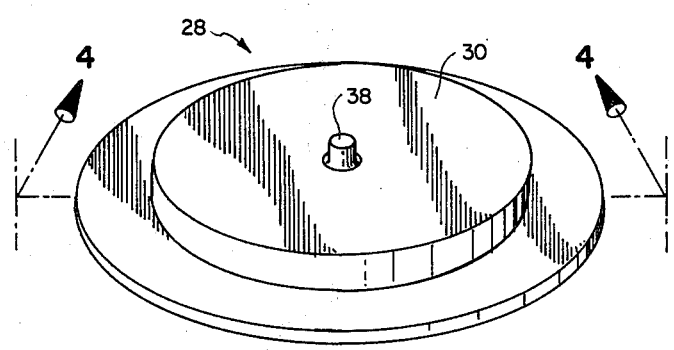
FIG. 3 is a perspective view of another embodiment of the invention.
Figure 4:
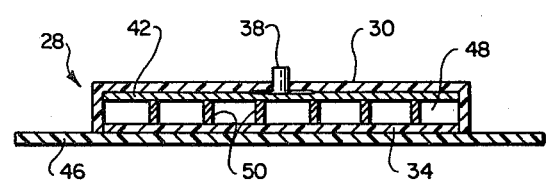
FIG. 4 is a side, cross-sectional view of the bioelectrode of FIG. 3.

FIGS. 3 and 4 show respectively a perspective view of another embodiment of the present invention and a side, cross-sectional view thereof. In this embodiment, a receptacle 28 for holding an ionic solution is formed of an upper wall 30 whose edges curve downwardly to join a bottom wall 34 (FIG. 4). The upper wall 30 is constructed of a flexible, deformable material such as polyurethane suitable for holding an ionic solution to be delivered through the skin or tissue of a person. The bottom wall 34 is composed of a porous, microporous, permeable or semipermeable membrane material such as microporous polycarbonate, microporous polytetrafluoroethylene or polyacrylonitrile, through which the ions in the solution can pass to the person's skin. This construction, as discussed thus far is disclosed in copending application, Ser. No. 963,029.

Disposed in the upper wall 30 of the bioelectrode 28 is a male part of a metallic snap 38 similar to that described for FIGS. 1 and 2. The nipple of the snap 38 projects from the upper surface of the wall 30 to make electrical contact with a corresponding female part of a snap (or other suitable conductor). The snap 38 includes a base portion which is positioned at the bottom surface of the upper wall 30 in contact with a conductive sheet of material 42 which is affixed to the bottom surface of the wall 30. Temporarily affixed to the bottom surface of the bottom wall 34 is a sanitary cover 46 which, when the bioelectrode is to be used, is simply peeled off. While in place, the cover 46 maintains the bottom wall 34 free from contamination.

Figure 5:
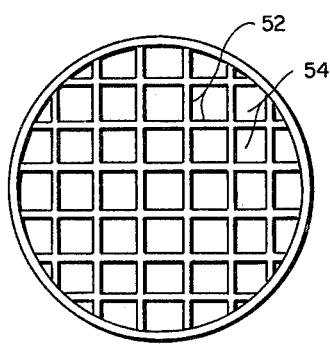
FIG. 5 is a top, cross-sectional view of one embodiment of the interior structure of the bioelectrode of FIG. 3.
Figure 6:
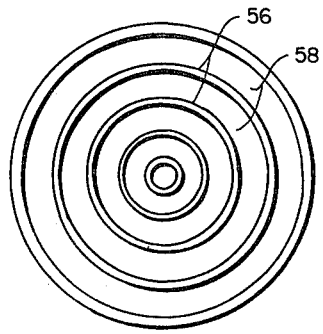
FIG. 6 is a top, cross-sectional view of another embodiment of the interior structure of the bioelectrode of FIG. 3.
Figure 7:
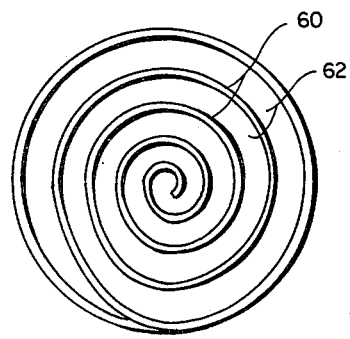
FIG. 7 is a top, cross-sectional view of still another embodiment of the interior structure of the bioelectrode of FIG. 3.

Disposed in the cavity 48 formed by the upper wall 30 and bottom wall 34 are a plurality of partition walls 50 which extend from the foil 42 to the bottom wall 34. The partition walls 50 may be arranged in a variety of shapes to generally prevent migration of ions laterally in the bioelectrode receptacle. Three examples of the formation of partition walls in the bioelectrode are shown in FIGS. 5, 6 and 7. In FIG. 5 partition walls 52 are shown in a grid pattern and define a plurality of separate, cube-shaped compartments 54. The material of the walls 52 is selected so as to prevent passage therethrough of the ions in the solution. Such material could be nonporous polyurethane. In FIG. 6, partition walls 56 are formed concentrically to define a plurality of annular compartments 58. The partition wall configuration of FIG. 5 prevents migration of ions in almost every lateral direction. The partition walls 56 in FIG. 6 prevent radial migration of ions but, of course, would not prevent a circumferential migration in each of the compartments. Other partition wall shapes, such as the spiral configuration of walls 60 shown in FIG. 7, could be devised to generally prevent lateral migration in the receptacle of the bioelectrode of FIGS. 3 and 4.

With the structure shown in FIGS. 3 through 7, ions are generally prevented from migrating in a direction parallel with the surface of the skin or tissue into which the ions are to be applied because of the positioning by the partition walls. Rather, the ions are constrained to migrate through the bottom wall 34 generally uniformly over the surface area of contact by the skin with the bottom wall. Also, with the configurations of FIGS. 3-7, a given compartment in a device is allowed to deplete itself of ions and force conduction through an adjacent compartment. Thus, when a given compartment is depleted of ions over a skin site of reduced impedance (i.e. burn, scratch, or other tissue damage) the movement to an adjacent site of conduction thus reduces the likelihood of a serious burn taking place or minimizes such burning or other tissue damage in the area of reduced tissue impedance. Indeed the depletion of ions from one region and the recruitment of an adjacent conduction site occurs throughout the iontophoretic treatment process in a continuous manner so that the total charge delivered to the skin is uniformly distributed to each area of the skin adjacent to the electrode surface. Such uniform current distribution and continuous recruitment of conduction sites operates to minimize iontophoretically induced burns.

In the manner described, iontophoretic bioelectrodes are provided wherein ion mobility is primarily limited to a direction normal to the surface of the skin or tissue into which the ions are to be applied. By so limiting the mobility of the ions, the likelihood of a concentration and delivery of ions at one or more points on the skin or tissue is avoided, and thus the likelihood of burns is reduced.

It should be understood that the above-defined embodiments are only illustrative of the application of the principles of the present invention and that numerous other alternative embodiments could be described without departing from the spirit and scope of the invention. For example, the partition walls 50 of the embodiment of FIGS. 3 and 4 could take a variety of shapes to prevent the lateral migration of ions. Also, various gel materials might be used in the FIGS. 1 and 2 embodiment so long as appropriate dimensions were selected for such material to stimulate the desired migration direction and inhibit the undesirable lateral migration. The appended claims are intended to cover all described embodiments and alternative embodiments which the present invention might have.

What is claimed is:

1. A bioelectrode for use in the iontophoretic delivery of ions into the skin or tissue of a person comprising
    means holding ions to be delivered, one side of which is for placement against the person's skin or tissue, said holding means being adapted to inhibit movement of ions in a direction generally parallel to the surface of the skin or tissue,
    an electrically conductive sheet of material disposed at a substantial portion of the other side of said holding means, and
    means for coupling said sheet of material to an electrical source.

2. A bioelectrode as in claim 1 wherein said holding means comprises an ion mobility inhibiting gel layer having a thickness-to-width ratio of about 0.1 or less.

3. A bioelectrode as in claim 2 wherein said gel layer is composed of a polysacharide gel.

4. A bioelectrode as in claim 2 wherein said gel layer is composed of Karaya gum.

5. A bioelectrode as in claim 2 further including a removable sheet of material covering said one side of the gel layer.

6. A bioelectrode as in claim 2 wherein said sheet of material is a flexible metal or metal-alloy foil.

7. A bioelectrode as in claim 2 wherein said gel layer includes a phosphate buffer.

8. A bioelectrode as in claim 7 wherein the ph of said gel layer is about six.

9. A bioelectrode as in claim 1 wherein said holding means comprises a receptacle having ion impermeable walls arranged to generally prevent migration of ions in a direction parallel to the surface of the skin or tissue.

10. A bioelectrode as in claim 9 wherein said walls are formed generally perpendicular to said one side of the receptacle to define a multiplicity of compartments therein, said compartments thereby allowing migration of ions from the other side of said receptacle to said one side but preventing migration laterally of the walls.

11. A bioelectrode as in claim 9 wherein said walls are formed generally perpendicular to said one side of the receptacle and in a spiral configuration to thereby allow migration of ions from the other side of said receptacle to said one side but prevent migration laterally of the walls.

12. A bioelectrode as in claim 9 wherein said walls are formed generally perpendicular to said one side of the receptacle and in generally concentric rings to thereby allow migration of ions from the other side of said receptacle to said one side but prevent migration laterally of the walls.

13. A bioelectrode as in claim 1 wherein said coupling means comprises the male part of a snap having
    a nipple which projects from the upper surface of said holding means, and
    a base portion joined to the nipple and electrically coupled to said sheet of material.

* * * * *